(12) United States Patent
Brodaczewski et al.

(10) Patent No.: US 10,709,448 B2
(45) Date of Patent: Jul. 14, 2020

(54) LINEAR CUTTER STAPLER

(71) Applicants: Wieslaw Mieczyslaw Brodaczewski, Dubai (AE); Andrzej Janusz Decewicz, Nottingham (GB); Konrad Gerard Brodaczewski, Dublin (IE)

(72) Inventors: Wieslaw Mieczyslaw Brodaczewski, Dubai (AE); Andrzej Janusz Decewicz, Nottingham (GB); Konrad Gerard Brodaczewski, Dublin (IE)

(73) Assignee: GRENA USA LLC, Wilmington, DE (US)

( * ) Notice: Subject to any disclaimer, the term of this patent is extended or adjusted under 35 U.S.C. 154(b) by 198 days.

(21) Appl. No.: 16/000,588

(22) Filed: Jun. 5, 2018

(65) Prior Publication Data
US 2018/0344320 A1  Dec. 6, 2018

Related U.S. Application Data (60) Provisional application No. 62/515,009, filed on Jun. 5, 2017.

(51) Int. Cl.
*A61B 17/072* (2006.01)
*A61B 17/32* (2006.01)

(52) U.S. Cl.
CPC .......... *A61B 17/07207* (2013.01); *A61B 2017/07214* (2013.01); *A61B 2017/07257* (2013.01); *A61B 2017/320052* (2013.01)

(58) Field of Classification Search
CPC .... A61B 17/07207; A61B 2017/07214; A61B 2017/07257; A61B 2017/320052
See application file for complete search history.

(56) References Cited

U.S. PATENT DOCUMENTS

| | | | | |
|---|---|---|---|---|
| 3,079,606 A | * | 3/1963 | Sergeevich | A61B 17/07207 227/76 |
| 3,317,105 A | * | 5/1967 | Vasiljevich | A61B 17/07207 227/76 |
| 3,490,675 A | | 1/1970 | Green | |
| 3,499,591 A | * | 3/1970 | Green | A61B 17/07207 227/76 |
| 4,429,695 A | | 7/1984 | Green | |
| 4,534,351 A | * | 8/1985 | Rothfuss | A61B 17/128 606/143 |

(Continued)

FOREIGN PATENT DOCUMENTS

EP 0517975 A1 12/1992

*Primary Examiner* — Nathaniel C Chukwurah
*Assistant Examiner* — Lucas E. A. Palmer
(74) *Attorney, Agent, or Firm* — Seth Natter; Natter & Natter (57) ABSTRACT

A linear cutter stapler includes an anvil jaw and a staple cartridge jaw. A post which projects from the anvil toward the staple cartridge includes a rounded crown dimensioned to self-seat in the cartridge. An abutment stop of the post abuts the cartridge to fix the spacing between the anvil and the cartridge when the jaws are closed. Alignment flanges, which project from the sides of the anvil, are received in notches formed in the sides of the cartridge jaw to stabilize the closed jaws. Both the post and the alignment flanges assure registration of staple shaping depressions formed in the anvil with the staples carried in the cartridge.

20 Claims, 8 Drawing Sheets

(56) References Cited

U.S. PATENT DOCUMENTS

| | | | | |
|---|---|---|---|---|
| 4,633,874 A * | 1/1987 | Chow | | A61B 17/07207 227/176.1 |
| 4,819,853 A * | 4/1989 | Green | | A61B 17/072 227/19 |
| 4,991,764 A * | 2/1991 | Mericle | | A61B 17/07207 227/178.1 |
| 5,221,036 A | 6/1993 | Takase | | |
| 5,307,976 A * | 5/1994 | Olson | | A61B 17/07207 227/175.3 |
| 5,403,312 A * | 4/1995 | Yates | | A61B 17/07207 606/50 |
| 5,452,837 A * | 9/1995 | Williamson, IV | | A61B 17/07207 227/176.1 |
| 5,485,947 A * | 1/1996 | Olson | | A61B 17/07207 227/176.1 |
| 5,551,622 A | 9/1996 | Yoon | | |
| 5,632,432 A * | 5/1997 | Schulze | | A61B 17/07207 227/176.1 |
| 5,814,055 A * | 9/1998 | Knodel | | A61B 17/07207 227/901 |
| 8,007,513 B2 | 8/2011 | Nalagatla | | |
| 8,978,954 B2 * | 3/2015 | Shelton, IV | | A61B 17/1155 227/175.1 |
| 9,522,029 B2 * | 12/2016 | Yates | | A61B 17/07207 |
| 10,390,826 B2 * | 8/2019 | Badawi | | A61B 17/072 |
| 2004/0094598 A1 * | 5/2004 | Geiste | | A61B 17/07207 227/180.1 |
| 2004/0164123 A1 * | 8/2004 | Racenet | | A61B 17/072 227/176.1 |
| 2005/0230453 A1 * | 10/2005 | Viola | | A61B 17/00491 227/176.1 |
| 2006/0111738 A1 * | 5/2006 | Wenchell | | A61B 17/00491 606/186 |
| 2007/0095877 A1 * | 5/2007 | Racenet | | A61B 17/072 227/175.2 |
| 2007/0194080 A1 * | 8/2007 | Swayze | | A61B 17/072 227/176.1 |
| 2009/0308907 A1 * | 12/2009 | Nalagatla | | A61B 17/07207 227/175.2 |
| 2011/0233261 A1 * | 9/2011 | Rao | | A61B 17/068 227/177.1 |
| 2012/0209314 A1 * | 8/2012 | Weir | | A61B 17/07207 606/205 |
| 2014/0239042 A1 * | 8/2014 | Simms | | A61B 17/07207 227/176.1 |
| 2014/0239043 A1 * | 8/2014 | Simms | | A61B 17/07207 227/176.1 |
| 2015/0374361 A1 * | 12/2015 | Gettinger | | A61B 17/07207 227/175.2 |
| 2015/0374363 A1 * | 12/2015 | Laurent, IV | | A61B 17/068 227/175.3 |
| 2015/0374373 A1 * | 12/2015 | Rector | | A61B 17/105 606/219 |
| 2016/0345971 A1 | 12/2016 | Bucciaglia | | |
| 2017/0095251 A1 * | 4/2017 | Thompson | | A61B 17/07207 |
| 2018/0235619 A1 * | 8/2018 | Harris | | A61B 17/07207 |
| 2018/0235630 A1 * | 8/2018 | Vulhop | | A61B 17/07292 |
| 2020/0046353 A1 * | 2/2020 | Deck | | A61B 17/07207 |

* cited by examiner

LINEAR CUTTER STAPLER

RELATED APPLICATIONS

This application claims the benefit of Provisional Application No. 62/515,009 filed Jun. 5, 2017, the entirety of which is incorporated herein by reference.

BACKGROUND OF THE INVENTION

1. Field of the Invention

This invention relates generally to surgical staplers and more specifically to linear cutter staplers.

2. Antecedents of the Invention

Linear cutter staplers have been employed in various surgical procedures such as gastrointestinal, thoracic, gynaecologic and paediatric surgery for the transection, resection and creation of anastomoses. Such staplers generally comprised a pair of pivotally joined jaws, with one jaw carrying a cartridge loaded with two parallel double rows of surgical staples and the other jaw comprising an anvil having two parallel double rows of staple clenching depressions. Both the anvil and the cartridge include a longitudinal knife channel separating the parallel double rows.

A staple seating wedge cam is positioned at the distal end of an actuating bar with a knife positioned behind the wedge. After the jaws are closed around a vessel or tissue to be stapled and cut, the actuating bar is advanced toward the distal ends of the jaws, the wedge cam engages follower lugs in the cartridge which drives successive staple ends through the vessel or tissue and into the clenching depressions. The wedge cam is followed by the knife, which cuts the vessel or tissue between the parallel double rows of clenched staples, as illustrated in U.S. Pat. No. 3,079,606, issued to Bobrov, et al, U.S. Pat. No. 3,490,675, issued to Green, et al, U.S. Pat. No. 4,991,764 issued to Mericle and U.S. Pat. No. 8,007,513 issued to Nalagatla, which are incorporated herein by reference in their entireties.

The prior cutter staplers were employed successfully in multiple surgical procedures over the years; however there existed a need for improving the alignment between the jaws when closed to assure precise registration between the individual staples of each row and the clinching depressions in the anvil as well as for stabilizing the closed jaws during advancement of the actuating bar. Additionally, there existed a need to assure proper spacing between the closed jaws.

Alignment issues were addressed in U.S. Pat. No. 3,079,606 by providing a sharp pointed pin at the distal end of the anvil jaw which seated in the knife channel of the cartridge adjacent its distal end and by providing cheek pieces on the sides of the cartridge carrying jaw which overlapped the sides of the anvil jaw adjacent the pivot.

Unfortunately the sharp pointed pin exhibited a tendency to tear, cut, abrade and otherwise traumatize surrounding tissue as the jaws were being closed and the need for stabilizing the jaws and assuring proper spacing remained.

SUMMARY OF THE INVENTION

A linear cutter stapler includes an upper jaw comprising an anvil and a lower jaw carrying a staple cartridge. A post adjacent the distal end of an anvil knife channel projects from the anvil toward the distal end of a cartridge knife channel. The post includes a rounded crown dimensioned to self-seat in the distal end of the cartridge knife channel for lateral alignment of the anvil and the cartridge. A shoulder of the post is dimensioned to abut the cartridge adjacent the knife channel to fix the spacing between the anvil and the cartridge when the jaws are closed.

Alignment flanges, which project from the sides of the anvil, are received in notches formed in the outer sides of the cartridge jaw to stabilize the closed jaws. Both the post and the alignment flanges assure registration of the staple shaping depressions formed in the anvil with the staples carried in the cartridge.

From the foregoing compendium, it will be appreciated that an aspect of the present invention is to provide a linear cutter stapler of the general character described which is not subject to the aforementioned disadvantages of the antecedents of the invention.

A feature of the present invention is to provide a linear cutter stapler of the general character described which staples and cuts vessels and tissue with but minimal trauma to adjacent tissue.

A consideration of the present invention is to provide a linear cutter stapler of the general character described which assures precise registration between staple clinching depressions of an anvil and rows of staples carried in a cartridge.

Another aspect of the present invention is to provide a linear cutter stapler of the general character described which may be employed by medical practitioners without difficulty.

A further feature of the present invention is to provide a linear cutter stapler of the general character described which is well suited for economical mass production fabrication.

An additional consideration of the present invention is to provide a linear cutter stapler of the general character described which is relatively simple to use.

To provide a linear cutter stapler of the general character described wherein parallel double rows of staples are precisely registered with staple clinching depressions is another aspect of the present invention.

An additional feature of the present invention is to provide a linear cutter stapler of the general character described having a pair of jaws which are precisely spaced from one another when closed.

An additional consideration of the present invention is to provide a linear cutter stapler of the general character described wherein a pair of opposed jaws are stabilized when closed to assure accurate stapling and cutting of vessels or tissue.

Other aspects, features and considerations of the present invention in part will be obvious and in part will be pointed out hereinafter.

With these ends in view, the invention finds embodiment in various combinations of elements, arrangements of parts and series f steps by which the above-mentioned aspects, features and considerations and certain other aspects, features and considerations are attained, or with reference to the accompanying drawings and the scope of which will be more particularly pointed out and indicated in the appended claims.

BRIEF DESCRIPTION OF THE DRAWINGS

In the accompanying drawings, wherein one of the various possible exemplary embodiments of the invention is shown.

DESCRIPTION OF THE INVENTION

The present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements.

Moreover, where certain elements of the present invention can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein.

Applicants do not intend for any term in the specification or claims to be ascribed an uncommon or special meaning unless explicitly set forth as such. Further, the present invention encompasses present and future known equivalents to the known components referred to herein by way of illustration.

Referring now in detail to the drawings, the reference numeral 10 denotes generally a linear cutter stapler constructed in accordance with and embodying the invention. The linear cutter stapler 10 comprises an upper jaw 12 pivotally joined to a lower jaw 14. Received within the lower jaw is a disposable staple cartridge 16 carrying two parallel double rows of surgical staples 18 separated by a longitudinal knife channel 20, illustrated in FIG. 9.

Figure 2:
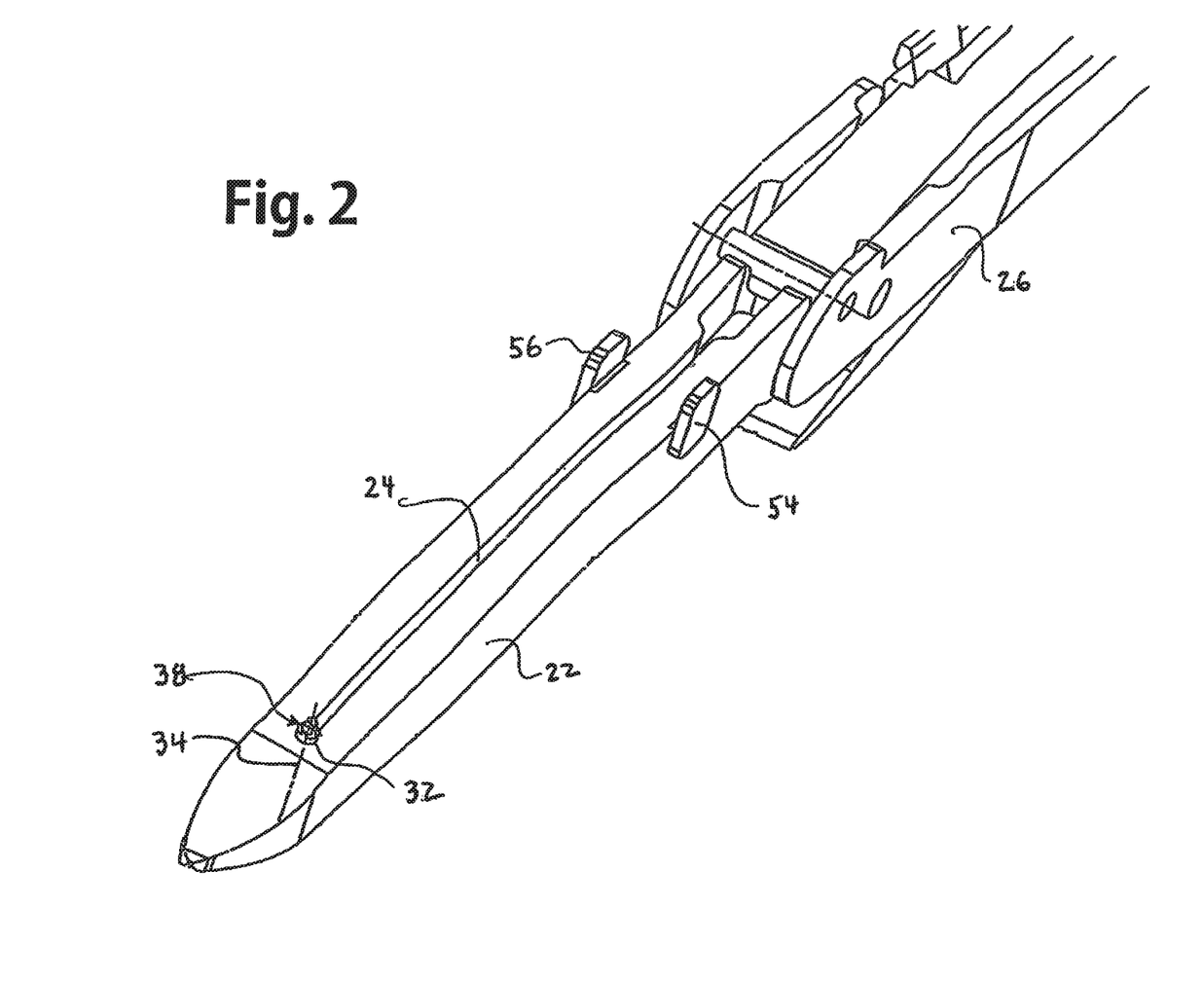
FIG. 2 is an enlarged scale isometric view of the underside of the anvil and showing a crowned post projecting from the anvil as well as a pair of alignment flanges projecting from the sides of the anvil.
Figure 4:
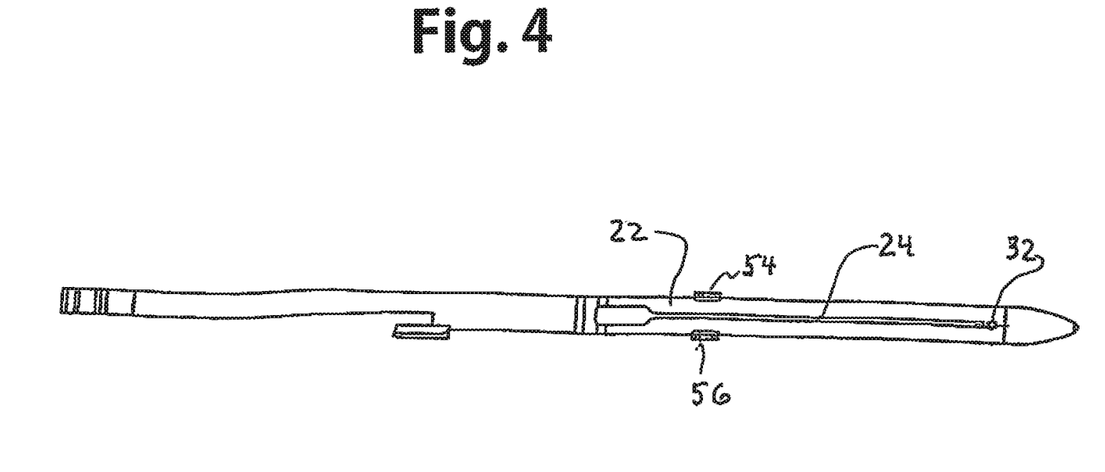
FIG. 4 is a bottom plan view of the anvil.

The upper jaw 12 comprises an anvil 22 having a longitudinal knife channel 24 and two parallel double rows of staple clinching depressions which have been omitted from FIG. 2 and FIG. 4 for clarity and which are depicted in FIG. 4 of U.S. Pat. Nos. 3,079,606 and 4,991,764 as well as FIG. 17 of U.S. Pat. No. 3,490,675 which have been incorporated herein by reference in their entireties.

In use, the disposable staple cartridge 16, containing the parallel double longitudinal rows of staples 18, is inserted into the lower jaw 14. The linear cutter stapler 10 is inserted through an incision or cavity in a patient's body and manipulated such that a vessel or tissue to be cut and sutured is positioned between the jaws 12, 14.

As described in U.S. Pat. Nos. 3,079,606 and 4,991,764, a staple seating wedge cam is positioned at the distal end of an actuating bar with a knife positioned behind the wedge. The jaws are closed by rotating a handle 26 having a locking latch 28. With the jaws clamped around a vessel or tissue to be stapled and cut, the actuating bar is pushed distally by advancing a knob 30 which is fixed to the actuating bar. The wedge cam engages successive follower lugs in the cartridge to drive successive staples through the vessel or tissue and into the clenching depressions, as illustrated in FIG. 17 of U.S. Pat. No. 3,490,675. The wedge cam is followed by the knife, which slides within the knife channels 20, 24 and severs the vessel or tissue between the parallel double rows of clenched staples.

The overall mode of operation aforementioned is fully described in one or more of the following U.S. Pat. Nos. 3,079,606, 4,429,695, and 4,991,764 and 8,007,513 and is embodied in the 55 mm Linear Cutter and the 75 mm Linear Cutter available from Ethicon, Inc., a subsidiary of Johnson and Johnson.

In accordance with the present invention, a cylindrical post 32, which is fixed adjacent the distal end of the anvil knife channel 24 projects from the anvil 22 toward the distal end of the cartridge knife channel 20.

The post 32 extends along a longitudinal axis 34 transverse to a longitudinal axis 21 of the anvil 22 and a longitudinal axis 23 of the lower jaw 14 and in registration with the distal end of the cartridge knife channel 20, when the jaws are substantially parallel.

Figure 5:
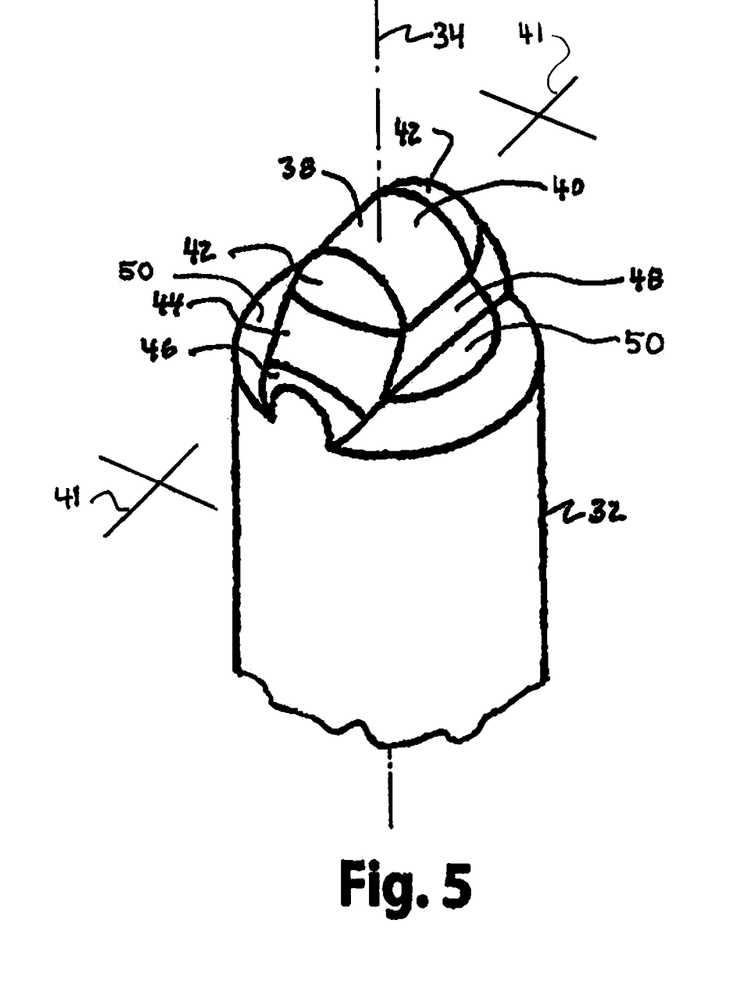
FIG. 5 is an enlarged scale isometric view of the post having a rounded crown tip.
Figure 6:
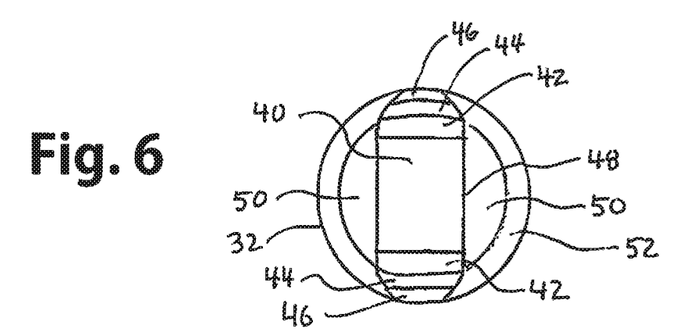
FIG. 6 is an enlarged scale bottom plan view of the post, showing the crown and an abutment plate which engages the cartridge to provide a limit stop when the jaws are closed.
Figure 7:
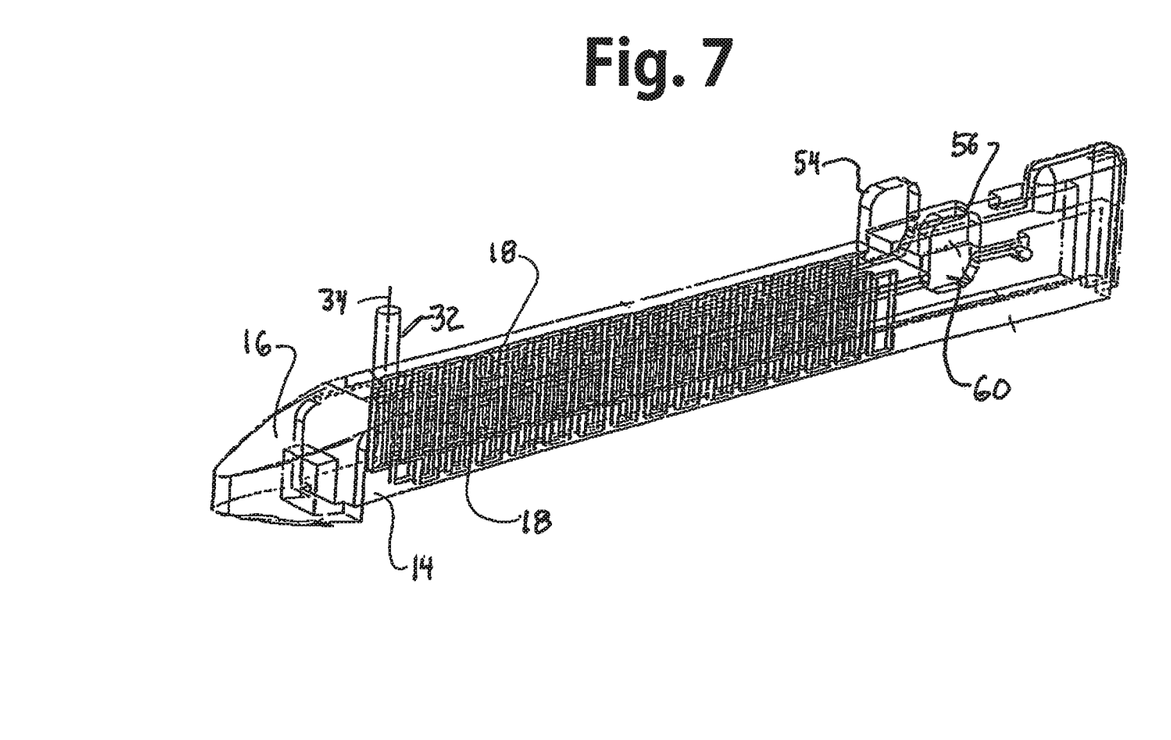
FIG. 7 is an isometric view of the lower jaw, in phantom, illustrating the staple cartridge loaded with surgical staples; also shown are the post and the alignment flanges which project downwardly from the sides of the anvil to be received in notches formed in the outer sides of the lower jaw; the remainder of the anvil is not illustrated.
Figure 9:
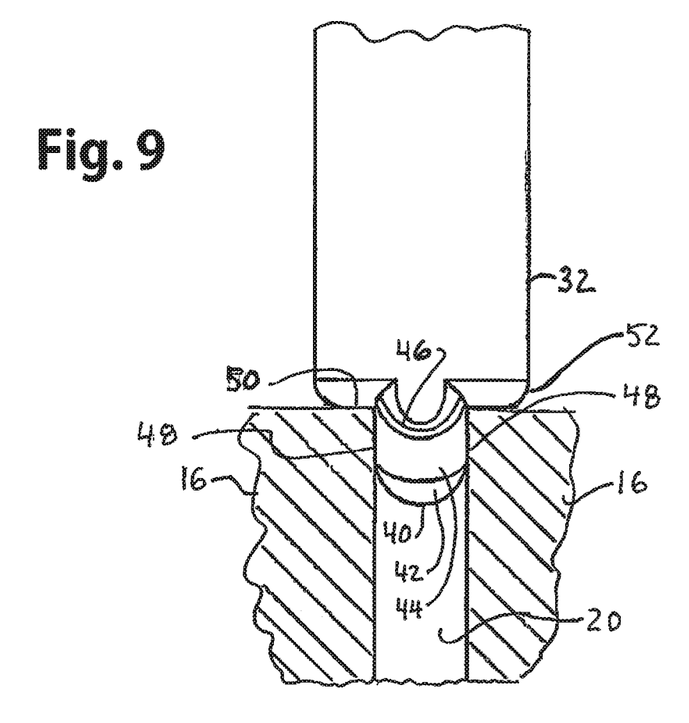
FIG. 9 is an enlarged scale fragmentary transverse sectional view, taken along the plane 9-9 of FIG. 8 and showing the post crown seated in the knife channel of the cartridge, with the abutment plate fixing the distance between the jaws; the remainder of the anvil has been omitted for clarity.

With reference to FIGS. 5, 6 and 9, it will be noted that the post 32 includes a smooth crown 38 comprising a cylindrical section 40 cut along a longitudinal axis 41 transverse to the longitudinal axis 34 of the post and parallel to the longitudinal axes 21, 23 of the anvil 22 and lower jaw 14 respectively. From the transverse ends of the cylindrical section 40, the crown surfaces are sloped outwardly toward the periphery of the post 32 at intermediate sections 42, 44, and 46 and terminate at diametrically opposed peripheral surfaces of the post 32.

The longitudinal side surfaces of the cylindrical section 40 transition into parallel planar walls 48 which terminate at transverse planar sections 50 configured as abutment stops for engaging the cartridge surfaces abutting the knife channel 20 to assure proper spacing between the anvil 22 and the cartridge 16. From the planar sections 50 a curved shoulder 52 extends to the cylindrical periphery of the post 32.

It should be noted that the maximum width of the cylindrical section 40 and the distance between the planar walls 48 is such that the crown 38 is snugly received in the cartridge knife channel 20, as illustrated in FIG. 9, while the cylindrical curvature and sloped intermediate sections 42, 44 and 46 assure self-seating in the channel 20, for true positioning and alignment of the anvil 22 and the cartridge 16.

Alignment of the anvil 22 and the cartridge 16 is also assured and/or supplemented by a pair of alignment flanges 54, 56, which project from the sides of the anvil 22. The flanges 54, 56, are received in notches 58, 60 formed in the outer sides of the lower jaw 14 to stabilize the jaws and ensure registration of each staple 18 carried in the cartridge 16 with its respective staple shaping depression so that when the staples 18 are fired, they will be received in their respective staple shaping depressions.

Figure 1:
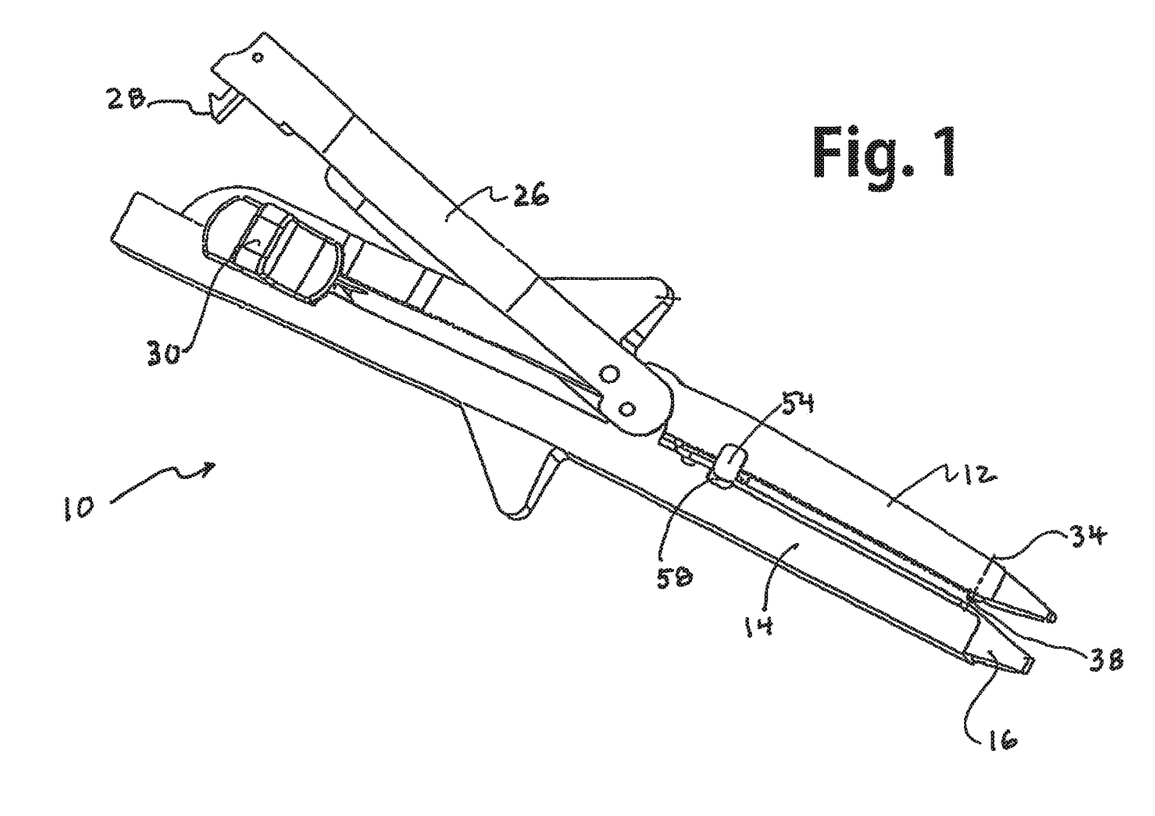
FIG. 1 is an isometric view of a linear cutter stapler in accordance with the invention having an upper jaw comprising an anvil and lower jaw carrying a staple cartridge.
Figure 3:
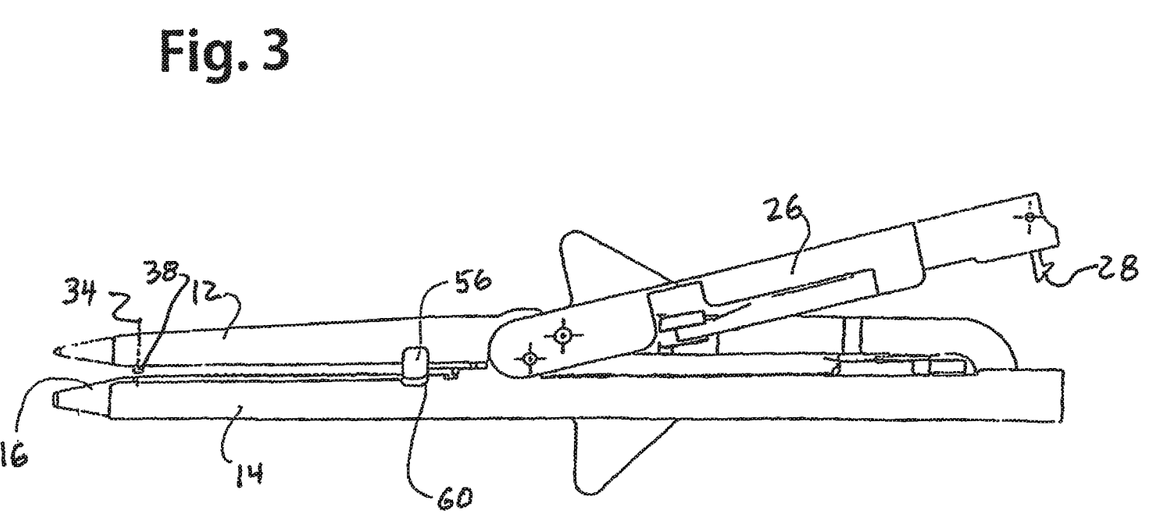
FIG. 3 is a side elevation view of the linear cutter stapler with the jaws partially closed.
Figure 8:
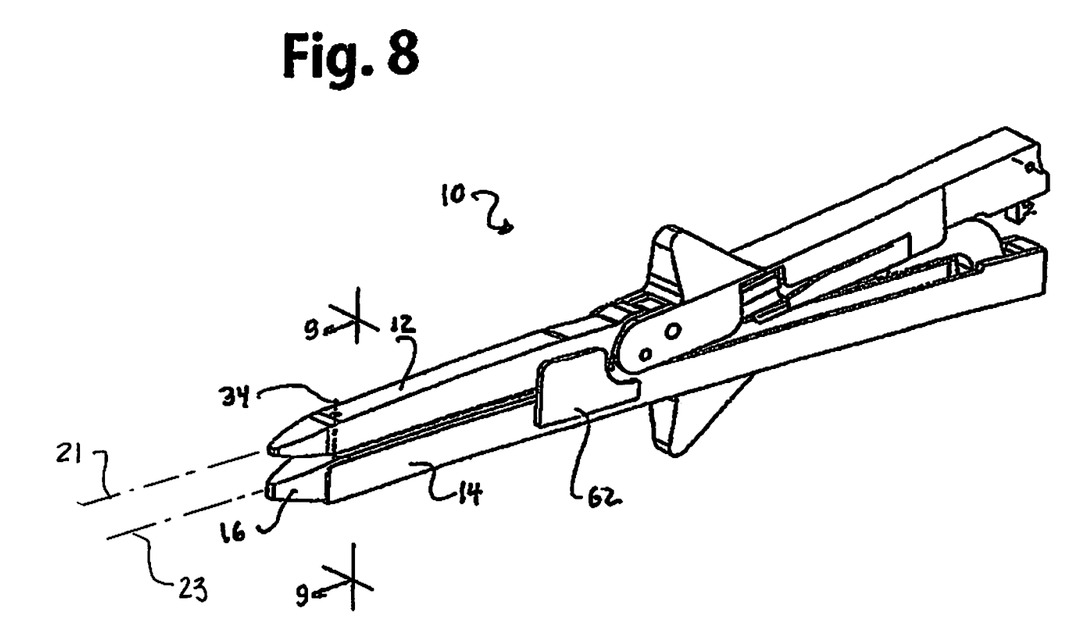
FIG. 8 is further isometric view of the linear cutter stapler with the jaws partially closed and illustrating one of a pair of tissue blockers which overlap the alignment flanges and which were omitted from the previous views to better illustrate the alignment flanges.

A tissue blocker 62 is affixed to each side of the lower jaw 14 and overlies the alignment flanges 54, 56. The tissue blacker 62 is illustrated in FIG. 8 but has been omitted in FIGS. 1 and 3 to better illustrate the alignment flanges 54, 56.

Thus it will be seen that there is provided a linear cutter stapler which achieves the various aspects, features and considerations of the present invention and which is well suited to meet the conditions of practical usage.

In the figures of this application, in some instances, a plurality of elements may be shown as illustrative of a particular element, and a single element may be shown as illustrative of a plurality of a particular elements. Showing a plurality of a particular element is not intended to imply that a system or method implemented in accordance with the invention must comprise more than one of that element or step, nor is it intended by illustrating a single element that the invention is limited to embodiments having only a single one of that respective element. Those skilled in the art will recognize that the numbers of a particular element shown in a drawing can, in at least some instances, be selected to accommodate the particular user needs.

The particular combinations of elements and features in the above-detailed embodiment are exemplary only; the interchanging and substitution of these teachings with other teachings in this application are also expressly contemplated. As those skilled in the art will recognize, variations, modifications, and other implementations of what is described herein can occur to those of ordinary skill in the art without departing from the spirit and the scope of the invention as claimed.

Further, in describing the invention and in illustrating embodiments of the invention in the figures, specific terminology, numbers, dimensions, materials, etc., are used for the sake of clarity. However the invention is not limited to the specific terms, numbers, dimensions, materials, etc. so selected, and each specific term, number, dimension, material, etc., at least includes all technical and functional equivalents that operate in a similar manner to accomplish a similar purpose. Use of a given word, phrase, number, dimension, material, language terminology, product brand, etc. is intended to include all grammatical, literal, scientific, technical, and functional equivalents. The terminology used herein is for the purpose of description and not limitation.

Having described the preferred embodiment of the invention, it will now become apparent to one of ordinary skill in the art that other embodiments incorporating the concept may be used. Moreover, those of ordinary skill in the art will appreciate that the embodiment of the invention described herein can be modified to accommodate and/or comply with changes and improvements in the applicable technology and standards referred to herein.

Variations, modifications, and other implementations of what is described herein can occur to those of ordinary skill in the art without departing from the spirit and the scope of the invention as claimed. It is felt therefore that these embodiments should not be limited to the disclosed embodiment but rather should be limited only by the spirit and scope of the appended claims.

Having thus described the invention there is claimed as new and desired to be secured by Letters Patent:

1. In a linear cutter stapler for surgical procedures, the linear cutter stapler comprising a pair of pivotally joined jaws, one jaw carrying a cartridge loaded with two parallel rows of surgical staples separated by a cartridge channel and the other jaw comprising an anvil having two parallel rows of staple clenching depressions separated by an anvil channel and a post projecting from the anvil toward the cartridge, the improvement comprising a smooth rounded crown formed at the end of the post, the post having a longitudinal axis and the smooth rounded crown comprising a cylindrical section having an longitudinal axis transverse to the longitudinal axis of the post, whereby tissue adjacent an operative site will not be cut, abraded, injured or subject to trauma otherwise caused by contact with the end of the post while the jaws are being closed.

2. The improved linear cutter stapler in accordance with claim 1 wherein at least a portion of the smooth rounded crown is configured to seat in the cartridge channel when the jaws are closed.

3. The improved linear cutter stapler in accordance with claim 1 wherein the improvement further comprises a planar alignment flange projecting from each side of the anvil toward the one jaw, the alignment flanges overlapping the sides of the one jaw when the jaws are closed.

4. The improved linear cutter stapler in accordance with claim 3 wherein each flange seats in a notch formed in each side of the one jaw.

5. The improved linear cutter stapler in accordance with claim 1 wherein the longitudinal axis of the cylindrical section is parallel to the anvil channel.

6. The improved linear cutter stapler in accordance with claim 1 wherein the cylindrical section includes transverse ends and the smooth rounded crown further comprises crown surfaces sloped from the transverse ends to the periphery of the post.

7. The improved linear cutter stapler in accordance with claim 1 wherein the cylindrical section includes side surfaces and the smooth rounded crown further comprises parallel planar walls dimensioned to seat in the cartridge channel when the jaws are closed, the side surfaces transitioning into the parallel planar walls.

8. The improved linear cutter stapler in accordance with claim 7 wherein the parallel planar walls terminate at an abutment stop comprising a transverse planar section of the post.

9. The improved linear cutter stapler in accordance with claim 8 wherein the abutment stop abuts the cartridge adjacent the channel of the cartridge when the jaws are closed, whereby proper spacing between the closed jaws is assured.

10. In a linear cutter stapler for surgical procedures, the linear cutter stapler comprising a pair of pivotally joined jaws, one jaw carrying a cartridge loaded with two parallel rows of surgical staples separated by a channel and the other jaw comprising an anvil having two parallel rows of staple clenching depressions separated by a channel and a post projecting from the anvil toward the channel of the cartridge, the improvement comprising a planar alignment flange projecting from each side of the anvil toward the one jaw, the flanges being received in notches formed in the outer face of each side of the one jaw.

11. The improved linear cutter stapler in accordance with claim 10, the improvement further comprising a smooth rounded crown formed at the end of the post, whereby tissue adjacent an operative site will not be cut, abraded, injured or subject to trauma otherwise caused by contact with the end of the post as the jaws are being closed.

12. The improved linear cutter stapler in accordance with claim 10, the improvement further comprising a tissue blocker overlying each of the alignment flanges when the jaws are closed.

13. The improved linear cutter stapler in accordance with claim 12 wherein the tissue blockers extend from the sides of the one jaw.

14. In a surgical device comprising a pair of pivotally joined jaws which close from an open position during a medical procedure at an operative site, one of the jaws having a longitudinal axis, a post adjacent a distal end of the one jaw, the other jaw being configured to receive at least a portion of the post, the improvement comprising a smooth rounded cylindrical section formed at the end of the post, the cylindrical section having a longitudinal axis parallel to the longitudinal axis of the one jaw, whereby tissue adjacent the operative site will not be cut, abraded, injured or subject to trauma otherwise caused by contact with the end of the post while the jaws are being closed.

15. The improved surgical device in accordance with claim 14 wherein the post includes a longitudinal axis and the smooth rounded crown comprises a cylindrical section lying transverse to the longitudinal axis of the post.

16. The improved surgical device in accordance with claim 15, wherein the cylindrical section includes transverse ends and the smooth rounded crown further comprises crown surfaces sloped from the transverse ends to the periphery of the post.

17. The improved surgical device in accordance with claim 15, wherein the cylindrical section includes side surfaces and the smooth rounded crown further comprises parallel planar walls, the side surfaces transitioning into the parallel planar walls.

18. The improved surgical device in accordance with claim 17, wherein the parallel planar walls terminate at abutment stops comprising transverse planar sections of the post.

19. The improved surgical device in accordance with claim 18, wherein the transverse planar sections engage the periphery of the post at a rounded shoulder.

20. The improved surgical device in accordance with claim 18, wherein the post is cylindrical.

* * * * *